(12) United States Patent
Baru

(10) Patent No.: US 7,282,980 B2
(45) Date of Patent: Oct. 16, 2007

(54) PRECISION RECTIFIER CIRCUIT FOR HIGH-DENSITY, LOW-POWER IMPLANTABLE MEDICAL DEVICE

(75) Inventor: Marcelo Baru, Burnaby (CA)

(73) Assignee: Neurostream Technologies, Inc., Port Coquitlam, British Columbia ( * ) Notice: Subject to any disclaimer, the term of this patent is extended or adjusted under 35 U.S.C. 154(b) by 0 days.

(21) Appl. No.: 10/935,699

(22) Filed: Sep. 7, 2004

(65) Prior Publication Data

US 2006/0109045 A1    May 25, 2006

Related U.S. Application Data

(63) Continuation of application No. 10/370,490, filed on Feb. 24, 2003, now abandoned.

(51) Int. Cl.
*H03L 5/00* (2006.01)
(52) U.S. Cl. .................. 327/330; 327/104; 363/44
(58) Field of Classification Search .............. 327/104, 327/330, 354; 363/44, 125, 127; 307/107, 307/127
See application file for complete search history.

(56) References Cited

U.S. PATENT DOCUMENTS

| 4,473,757 A | 9/1984 | Fargo et al. |
| 4,750,499 A | 6/1988 | Hoffer |
| 5,173,849 A | 12/1992 | Brooks |
| 5,306,968 A | 4/1994 | Kimura |
| 5,691,658 A | 11/1997 | Klein |
| 5,999,849 A | 12/1999 | Gord et al. |
| 6,469,561 B2 | 10/2002 | Pernigotti et al. |

FOREIGN PATENT DOCUMENTS

| EP | 0389515 B1 | 4/1996 |
| EP | 0976420 A1 | 2/2000 |
| EP | 0974377 B1 | 4/2002 |
| WO | WO89/05058 | 6/1989 |
| WO | WO96/28879 | 9/1996 |

OTHER PUBLICATIONS

R. Gregorian and C.G. Temes, "Analog MOS Integrated Circuits for Signal Processing", John Wiley & Sons, 1986, pp. 131-133.
K. Hayatleh et al. "Degradation Mechanisms in Operational Amplifier Precision Rectifiers" IEE Transactions on Circuits and Systems-I: Fundamental Theory and Applications, vol. 42, No. 8, Aug. 1995, pp. 479-485.

(Continued)

*Primary Examiner*—Kenneth B. Wells
(74) *Attorney, Agent, or Firm*—Seyfarth Shaw LLP

(57) ABSTRACT

A precision voltage rectifier comprises a source voltage input and a voltage reference. The rectifier comprises switching elements that, according to the sign of the source signal, change the connections to the inputs of a differential difference amplifier that is connected as a voltage inverter. Embodiments of the invention are fully-integrated and CMOS compatible with high-input impedance such that the invention can be operated in low-power situations. A preferred application involves the integration of several similar circuits in a high-density, low-power implantable medical device. Particular embodiments of the invention can be used to rectify nerve signals collected by electrodes for use in a system for manipulating a prosthetic device.

10 Claims, 10 Drawing Sheets

OTHER PUBLICATIONS

Paul D. Walker and Michael M. Green, "CMOS Half-Wave and Full Wave Precision Voltage Rectification Circuits" IEE, 1996, pp. 901-904.

A. arnaud et al., "Design of a Micropower Signal Conditioning Circuit for a Peizoresistive Acceleration Sensor", IEEE International Symposium on Circuits and Systems, vol. 1, 1998, pp. 269-272.

US 7,282,980 B2

PRECISION RECTIFIER CIRCUIT FOR HIGH-DENSITY, LOW-POWER IMPLANTABLE MEDICAL DEVICE

CROSS-REFERENCE TO RELATED APPLICATION

This is a continuation of U.S. patent application Ser. No. 10/370,490, filed Feb. 24, 2003, now abandoned the benefit of the filing date of which is hereby claimed under 35U.S.C. § 120.

TECHNICAL FIELD

This invention relates to the rectification of low voltage electrical signals. The invention has application as a precision rectifier circuit for high-density and low-power devices, for example implantable medical devices. Embodiments of the invention may be used to rectify bioelectrical signals.

BACKGROUND

Closed-loop Functional Electrical Stimulation (FES) devices generally require feedback information based on the "energy" contents of a sensed signal. Such feedback information may be obtained by detecting and amplifying selected bioelectrical signals. Circuitry for preconditioning signals to be used for feedback control typically includes a band-pass amplification circuit, a rectifier circuit and a bin-integration circuit. This circuitry provides a smoothed profile of the sensed activity. A rectifier circuit is needed because bioelectrical signals are typically alternating current (AC) signals. Such signals typically have low amplitudes. It is not uncommon for such signals to have amplitudes of less than 10 µV peak or even less than 3 µV peak. A voltage in AC signals oscillates with positive and negative excursions relative to a reference voltage level, typically the system ground. Rectification involves reversing the polarity of either the positive or negative going excursions, such that the rectified signal is comprised of a single polarity, either positive or negative.

In many applications, several different signals are simultaneously needed to control a prosthetic device; see for example U.S. Pat. No. 4,750,499 to Hoffer for a "Closed-Loop, Implanted-Sensor, Functional Electrical Stimulation System for Partial Restoration of Motor Functions". This translates into the need for several rectifier circuits to be integrated into the same implantable device. Consequently, a suitable rectifier circuit should consume minimum power and preferably use no external components.

FIG. 1 shows a prior art high-impedance continuous-time precision full-wave rectifier circuit 20. Circuit 20 comprises two operational amplifiers (A1, A2). Diodes (D1, D2) within the feedback path provide the necessary non-inverting gain for positive source signals and inverting gain for negative source signals. Such circuits have drawbacks that prevent their use in a high-density, low-power closed-loop FES implantable device. These drawbacks include the following:

i) Distortion due to the fact that the diode (D1) feedback path becomes open circuit around the zero-crossing, resulting in a missing segment in the output waveform for a time interval ($t_d$); see K. Hayatleh et al., "*Degradation Mechanisms in Operational Amplifier Precision Rectifiers*", IEEE Transactions on Circuits and Systems-I: Fundamental Theory and Applications, vol. 42, no. 8, August 1995, pp. 479-485;

ii) When i) occurs, the input is not driven sufficiently strongly to achieve the slew rate of the first amplifier (A1), and so the first amplifier (A1) operates in the linear region, typically resulting in a value of $t_d$ about an order of magnitude larger. The first amplifier (A1) therefore consumes unnecessary power.

iii) If resistors (R) were fully integrated, they would have to be large in order to keep the power consumption low. This would occupy a large die area;

iv) Two operational amplifiers (A1, A2) are needed; and, v) Standard CMOS technology does not provide the floating diodes required by circuit 20.

Two different prior art circuits that overcome some of the limitations of the circuit of FIG. 1 were disclosed by Kimura in 1994; see U.S. Pat. No. 5,306,968 to Kimura for a "*Rectifier Circuit Not Using Clock Signal*"; and by A. Arnaud et al. in 1998; see A. Arnaud et al., "*Design of a Micropower Signal Conditioning Circuit for a Peizoresistive Acceleration Sensor*", IEEE International Symposium on Circuits and Systems, vol. I, 1998, pp. 269-272.

FIG. 2 shows a prior art rectifier circuit 21 as disclosed by Kimura. The circuit comprises a polarity judgment circuit (C), a gain control circuit 22, a first amplifier 23, and a second amplifier 24. The signal to be rectified ($V_{in}$) is connected to the polarity judgment circuit (C) and the first amplifier 23. According to the output of the polarity judgment circuit (C), the gain-control circuit 22 provides two DC signals ($V_H$, $V_L$) to the second amplifier 24. These DC signals control the gain of the second amplifier 24. The output ($V_{out}$) is an amplified and rectified version of the source signal ($V_{in}$). Some disadvantages of circuit 21 are that several auxiliary DC voltages are needed to achieve rectification and that the gain of rectifier circuit 21 is highly dependent on process parameters.

FIG. 3 shows a prior art rectifier circuit 25 as disclosed by A. Arnaud et al. Circuit 25 operates in a manner similar to circuit 21. Here, a signal from polarity judgment circuit (C), is used to change the configuration of the operational amplifier (A) from an inverting amplifier to a follower and vice-versa according to the polarity of the input ($V_{in}$), using the switches 26 and inverter (T). A main disadvantage of circuit 25 that prevents implementation in a high-density, low-power device is that it requires two resistors (R). Resistors (R) need to be external in order for power consumption to be minimized. Another important disadvantage of circuit 25 is that it does not present sufficiently high input impedance if resistors (R) have values small enough that they can be practically integrated.

Weijand, European Patent No. 0 974 377 B1 ('377 patent) entitled "Full-wave Rectifier with Dynamic Bias" discloses a full-wave rectifier that is powered through movement or motion such as for use in pulse generation in a pacemaker. The Weijand device provides a full-wave rectifier circuit for rectification of a supply voltage on the order of one to three volts, or a frequency signal in the kHz range or higher, or both. The Weijand device uses four diodes implemented using field-effect transistors ("FETs"), which operate essentially as switches that turn on or off depending upon the voltage applied to control input gates. Weijand discloses that the voltage on one node must be slightly greater than the voltage on a second node, on the order of 10 to 15 mV, to reach an equilibrium wherein a FET turns off. Accordingly, Weijand discloses a threshold voltage of 10 to 15 mV, which is substantially less than the typical 0.7 V threshold voltage of conventional diodes. This threshold voltage is still too high to be suitable for rectifying low level bioelectrical signals.

Weijand, European Patent Application No. 0 976 420 A1 ('420 application) entitled "Movement Powered Timepiece Having a Full-wave Rectifier with Dynamic Bias" discloses a timepiece with a pulse generator which features a full-wave rectifier circuit which has a dynamic bias, such as the '377 patent. As with the '377 patent, the '420 application discloses a threshold voltage of 10 to 15 mV. Again, this is too high a threshold to be suitable for low level bioelectrical signals.

U.S. Pat. No. 5,173,849 to Brooks for "Integratable Synchronous Rectifier" discloses a rectifier that is integratable into VLSI "chip" form (such as NMOS or CMOS) for use in devices such as "smart" credit cards and identification devices.

U.S. Pat. No. 5,691,658 to Klein for "Current Mode Amplifier, Rectifier and Multi-Function Circuit" discloses amplifier circuits, a full-wave rectifier, a comparator, and a filter, all operating with current signals.

U.S. Pat. No. 5,999,849 to Gord et al. for "Low Power Rectifier Circuit for Implantable Medical Device" discloses a switched rectifier circuit that is realized using P-MOS and N-MOS FET switches that are turned on/off by a detector and inverter circuit. Parasitic diodes and transistors form an integral part of the FET circuitry to respond to and rectify the incoming signal during start up.

U.S. Pat. No. 4,473,757 to Farago et al. for "Circuit Means for Converting a Bipolar Input to a Unipolar Output" discloses a plurality of switching elements, preferably MOS transistors, connected in a bridge circuit. The bridge circuit has a pair of input terminals and a pair of output terminals, the input terminals receive an input signal of bipolar polarity for providing an output signal of a given polarity on the output terminals.

PCT Application No. WO 96/28879 of Scheelen for "Integrated Circuit Full-Wave Rectifier" discloses a full-wave rectifier circuit that is suitable for high power conversion, using voltage limiting means to allow voltage sensitive CMOS technology to be used. The Scheelen circuit can provide a direct connection to a source of voltage between 40 and 100 V, and may even be used at voltages up to 1100 V, including 600 V which is conventionally used for train and tram supplies.

The inventor has determined that there remains a need for a rectifying circuit with a low threshold voltage that can be fully integrated. There is a particular need for rectifying devices which are suitable for use in implantable biomedical devices, such as implantable systems for monitoring nerve signals for the control of prosthetic devices.

SUMMARY OF THE INVENTION

One aspect of the invention provides a signal rectifying circuit comprising a source signal input connected to a first input of a polarity judgment circuit and to a first input of a switching circuit. A reference signal is connected to a second input of the polarity judgment circuit and to a second input of the switching circuit. The polarity judgment circuit has an output connected to a first control input of the switching circuit. The switching circuit has a first output connected to a first non-inverting input of a differential difference amplifier ("DDA"), and a second output connected to a first inverting input of the DDA. The reference signal is further connected to a second non-inverting input of the DDA. The DDA has an output connected to a second inverting input of the DDA.

Another aspect of the invention provides a method for rectifying a source signal. The method comprises comparing a source signal voltage with a reference signal voltage. When the voltage of the source signal is greater than the voltage of the reference signal, the reference signal is connected to a first non-inverting input of a DDA, and the source signal is connected to a first inverting input of the DDA. When the voltage of the source signal is less than the voltage of the reference signal, the source signal is connected to the first non-inverting input of the DDA and the reference signal is connected to the first inverting input of the DDA.

BRIEF DESCRIPTION OF DRAWINGS

In Figures which illustrate non-limiting embodiments of the invention:

FIG. 5A is a schematic diagram showing of the signals connected to the DDA when a first set of switching elements is turned on;

FIG. 5B is a schematic diagram showing of the signals connected to the DDA when a second set of switching elements is turned on;

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
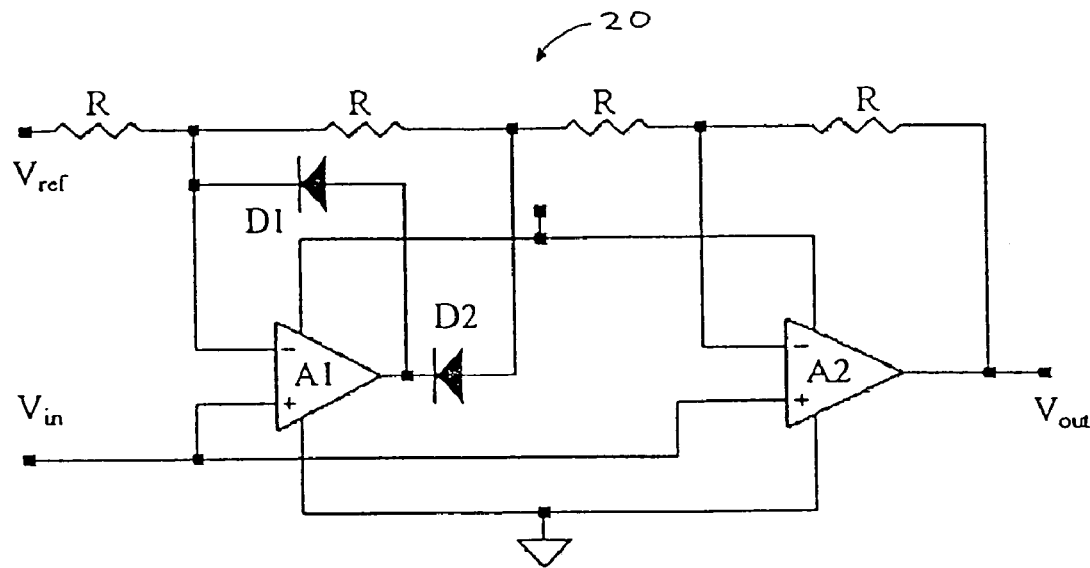
FIG. 1 is a schematic diagram showing a prior art high-impedance, continuous-time full-wave rectifying circuit.
Figure 2:
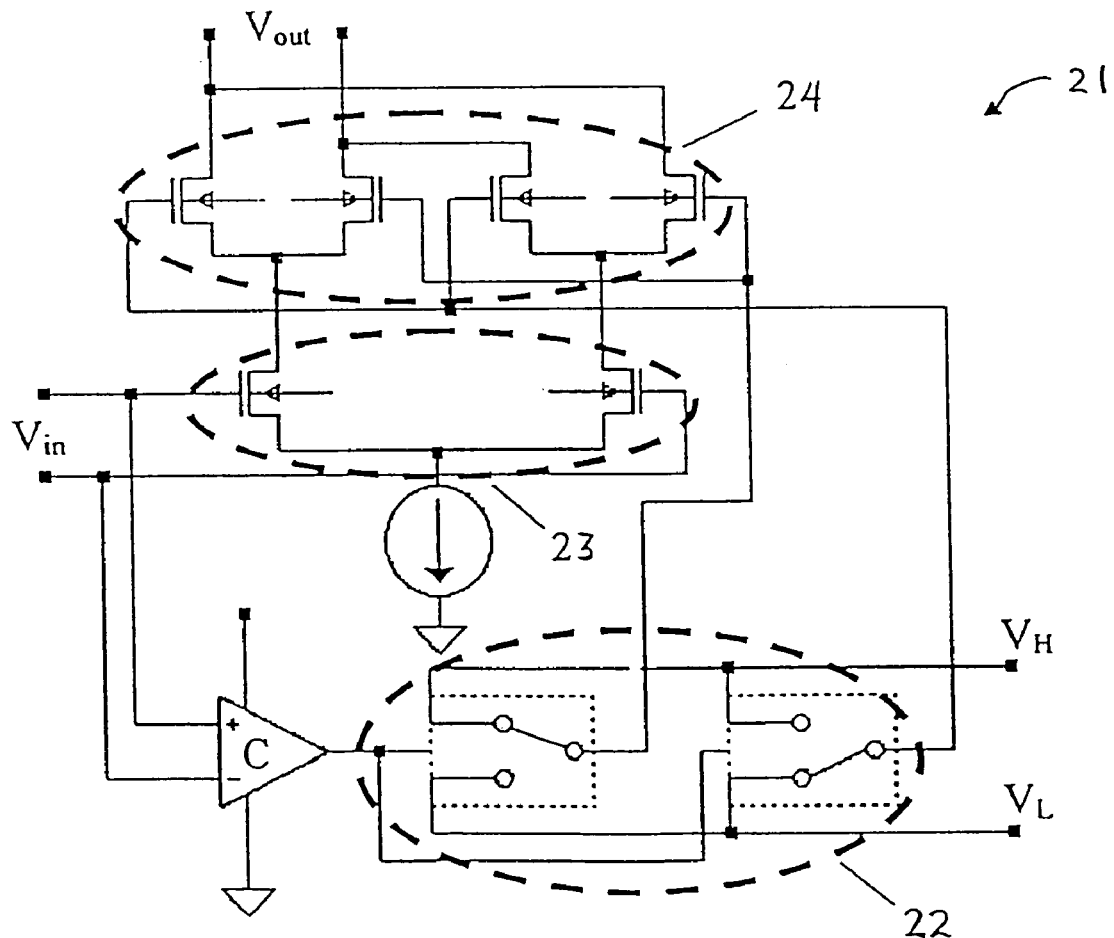
FIG. 2 is a schematic diagram showing a prior art high-impedance, continuous-time full-wave rectifying circuit.
Figure 3:
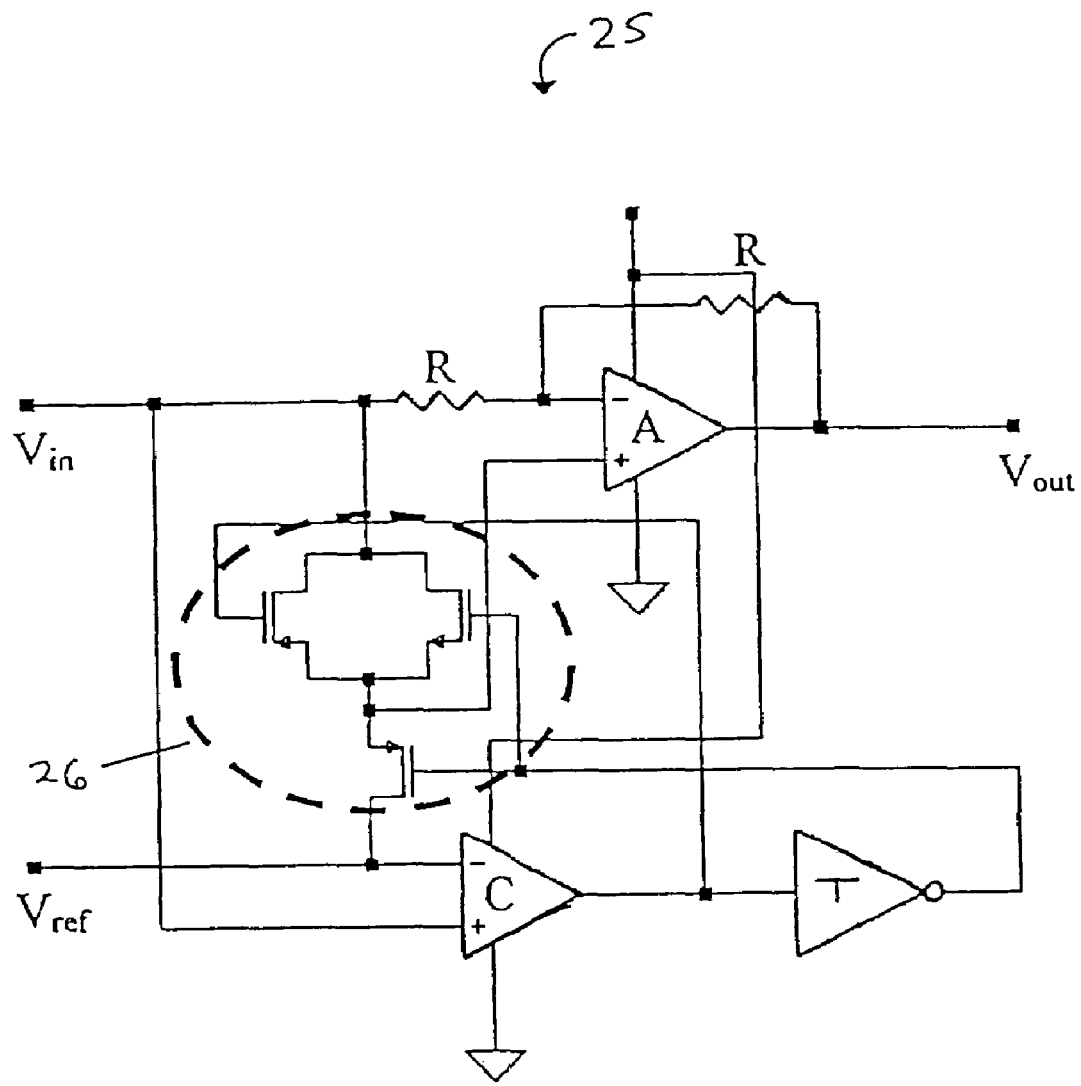
FIG. 3 is a schematic diagram showing a prior art continuous-time full-wave rectifying circuit.
Figure 4:
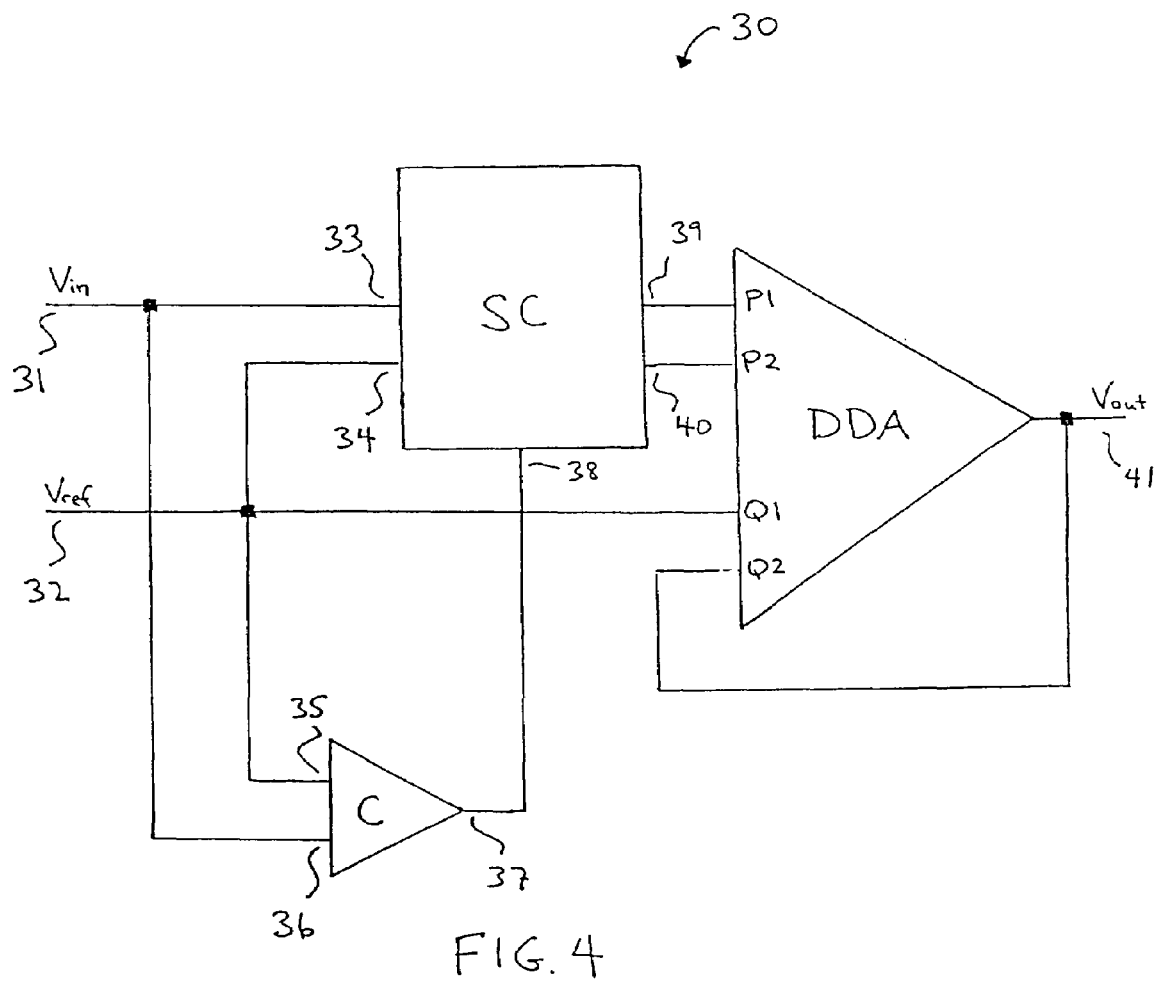
FIG. 4 is a schematic diagram showing of a continuous-time rectifying circuit according to one embodiment of the invention.

FIG. 4 is a schematic of a continuous-time rectifying circuit 30 according to the invention. In circuit 30, a first input 31 carrying a source signal ($V_{in}$) is connected to a first input 33 of a switching circuit (SC) and to a first input 36 of a polarity judgment circuit (C). A second input 32 carrying a reference signal ($V_{ref}$), is connected to a second input 34 of the switching circuit (SC) and to a second input 35 of the polarity judgment circuit (C).

A reference signal ($V_{ref}$) may be provided by any suitable source of reference voltage including a suitable voltage divider, voltage regulator, external voltage standard, a conductor which is at a known potential, etc. Output 37 of polarity judgment circuit (C) is connected to a control input 38 of switching circuit (SC). A first output 39 of switching circuit (SC) is connected to a first non-inverting input (P1) of a differential difference amplifier ("DDA"). A second output 40 of switching circuit (SC) is connected to a first inverting input (P2) of the DDA. The second input 32 is also connected to a second non-inverting input (Q1) of the DDA. An output 41 of the DDA is connected to a second inverting input (Q2) of the DDA.

Figure 5A:
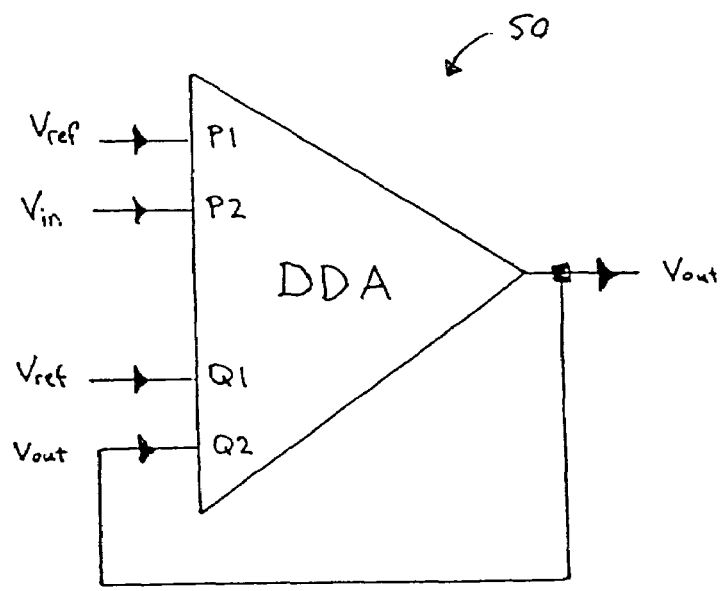
Figure 5B:
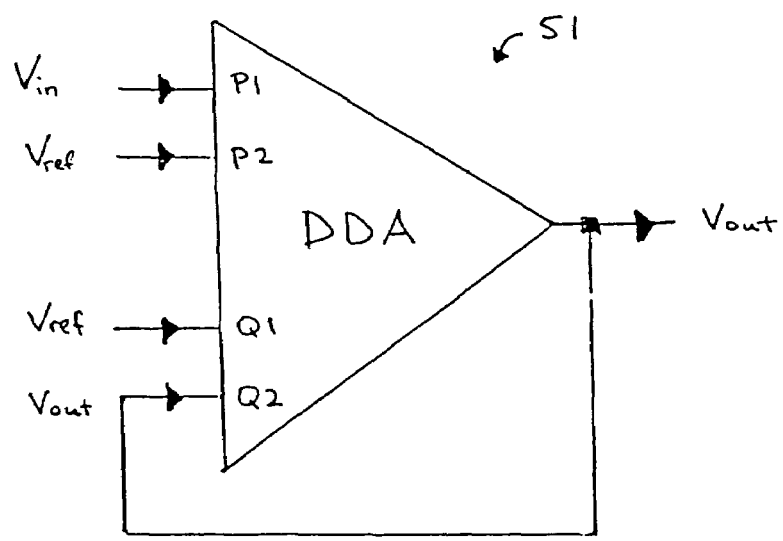

FIGS. 5A and 5B indicate the signals provided to each input terminal of the DDA during different phases of the operation of circuit 30. FIG. 5A shows a first connection pattern 50 in which switching circuit (SC) is in a first state and connects reference signal ($V_{ref}$) to the first non-inverting input (P1) of the DDA and source signal ($V_{in}$) to the first inverting input (P2) of the DDA. Together the first and second inputs (P1, P2) comprise a first differential pair of the DDA. FIG. 5A further shows the reference signal ($V_{ref}$) connected to a second non-inverting input (Q1), and the output signal ($V_{out}$) connected to a second inverting input (Q2) of the DDA. The second non-inverting input (Q1) and the second inverting input (Q2) together comprise a second differential pair of the DDA. FIG. 5B shows a second connection pattern 51 in which switching circuit (SC) is in a second state and connects source signal ($V_{in}$) to first input (P1) of the DDA and reference signal ($V_{ref}$) to second input (P2) of the DDA. The connections to the second differential pair (Q1, Q2) are the same in FIGS. 5A and 5B.

Switching circuit (SC) alternates between its two states to provide DDA connection patterns 50 and 51 depending upon whether the source signal ($V_{in}$) is more positive than or less positive than the reference signal ($V_{ref}$) as determined by polarity judgment circuit (C). For example, when the source signal ($V_{in}$) is at a potential which is more positive than the reference signal ($V_{ref}$), configuration pattern 50 is selected. When the source signal ($V_{in}$) is at a potential which is more negative than the reference signal ($V_{ref}$), configuration pattern 51 is selected. For positive half-wave rectification, when source signal ($V_{in}$) is more negative than reference signal ($V_{ref}$), a third configuration pattern may be selected in which reference signal ($V_{ref}$) is connected to both inputs (P1, P2) of the first differential pair, and the second differential pair remains as connected in FIGS. 5A and 5B.

Figure 6:
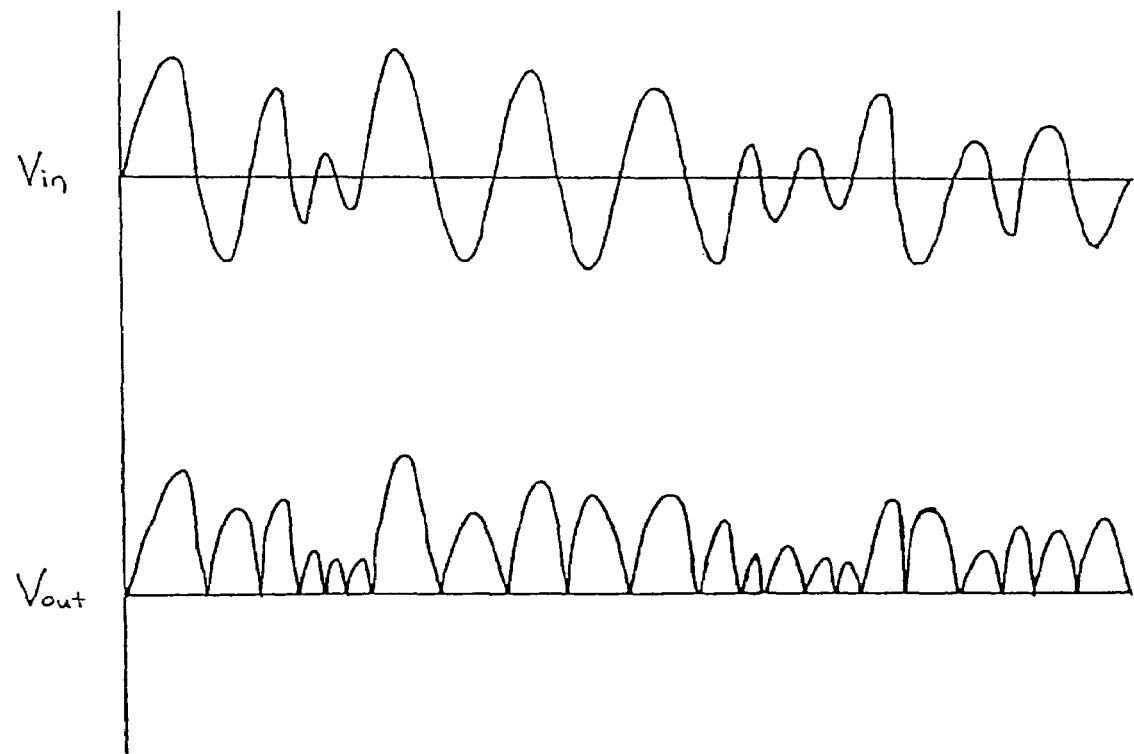
FIG. 6 is a representation of the voltage levels of a source signal ($V_{in}$) and an output signal ($V_{out}$) for a full-wave embodiment of the present invention.

FIG. 6 is a wave representation of the voltage values of the source signal ($V_{in}$) and the output signal ($V_{out}$) for a positive full-wave rectification embodiment of the invention.

Figure 7:
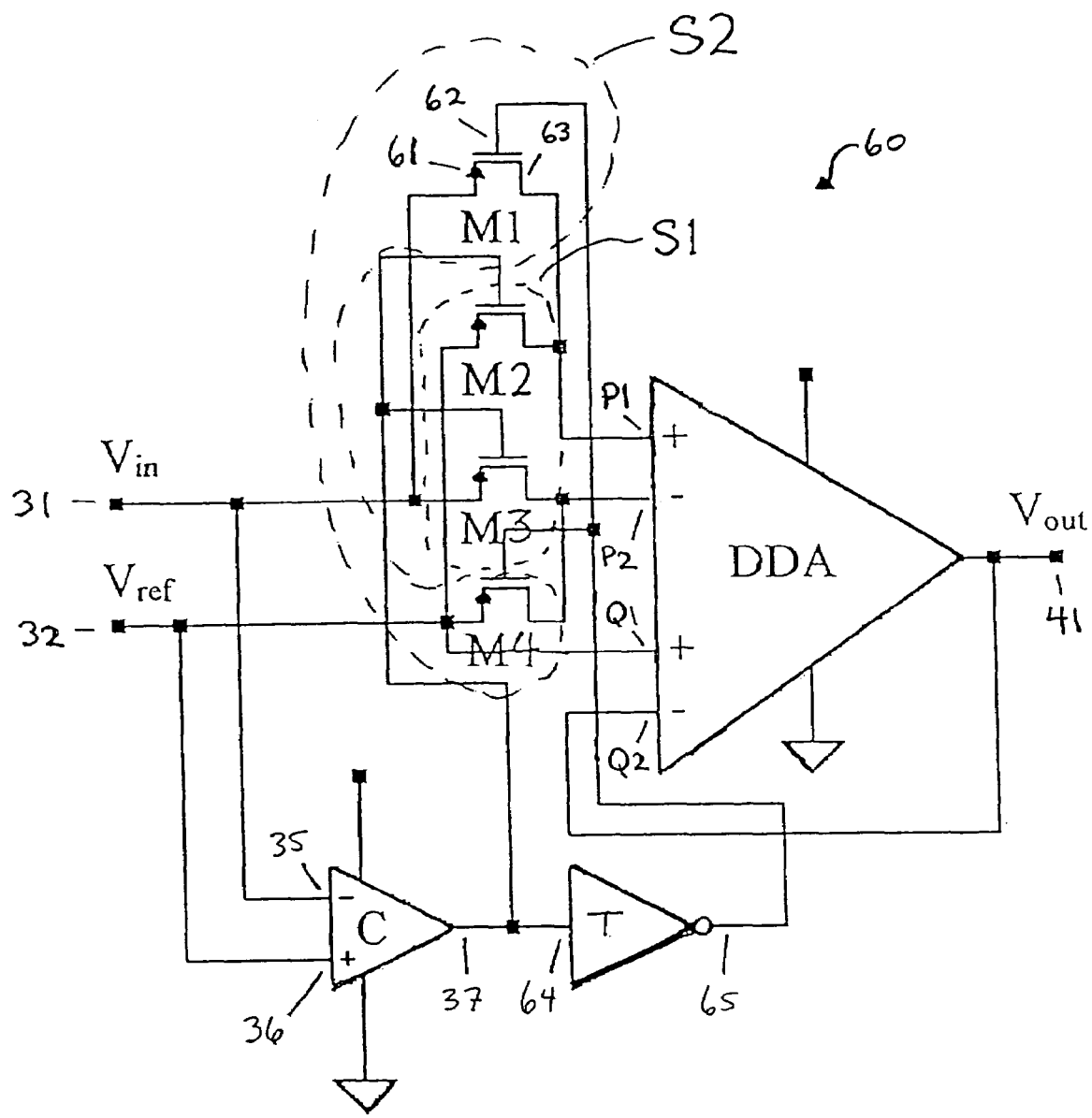
FIG. 7 is a schematic diagram showing an embodiment of a continuous-time full-wave rectifying circuit of the invention.

FIG. 7 shows a high-impedance, continuous-time full-wave rectifying circuit 60 according to a first preferred embodiment of the invention. In circuit 60, first input 31 carrying a source signal ($V_{in}$) is connected to a source 61 of a first switching element comprising a first FET (M1), to a source of a third switching element comprising a third FET (M3), and to an inverting input 35 of a polarity judgment circuit (C). Second input 32 carrying reference signal ($V_{ref}$) is connected to the sources of second and fourth switching elements comprising second and fourth FETs (M2, M4), to the non-inverting input 36 of the polarity judgment circuit (C), and to the non-inverting input (Q1) of the second differential pair of the DDA. The output signal ($V_{out}$) of the DDA is fed back to the inverting input (Q2) of this second differential pair.

A drain 63 of the first switching element (M1) and a drain of the second switching element (M2) are connected to the non-inverting input (P1) of the first differential pair of the DDA. A drain of the third switching element (M3) and a drain of the fourth switching element (M4) are connected to the inverting input (P2) of this first differential pair of the DDA. The output 37 of the polarity judgment circuit (C) is connected to the input 64 of an inverter (T) and to a gate of the second switching element (M2) and a gate of the third switching element (M3). The complementary output 65 of the polarity judgment circuit (C) is provided by inverter (T) and is connected to a gate 62 of the first switching element (M1) and a gate of the fourth switching element (M4).

In FIG. 7, the second (M2) and third (M3) switching elements together comprise a first switch set (S1), and the first (M1) and fourth (M4) switching elements together comprise a second switch set (S2). When the source signal ($V_{in}$) is more positive than the reference signal ($V_{ref}$), the output 37 of the polarity judgment circuit (C) has a low logical level. This causes the switches of the first switch set (S1) to be turned on and the switches of the second switch set (S2) to be turned off. Consequently, the reference signal ($V_{ref}$) is connected to the first non-inverting input (P1) of the DDA, and the source signal ($V_{in}$) is connected to the first inverting input (P2) of the DDA. When source signal ($V_{in}$) has a voltage less than the reference voltage then the switches of switch set (S1) are turned off and the switches of switch set (S2) are turned on so that the inputs of the DDA which ($V_{in}$) and ($V_{ref}$) are connected are reversed.

Another embodiment of the invention provides a continuous-time, precision half-wave rectifier. A half-wave rectifier according to the invention may be implemented by, for example, connecting the source of the first switching-element (M1) to the reference signal ($V_{ref}$), instead of to the source signal ($V_{in}$), for positive half-wave rectification. Negative half-wave rectification can be achieved by following the schematic of FIG. 7 but connecting the source of the third switching element (M3) to the reference signal ($V_{ref}$), instead of to the source signal ($V_{in}$).

Figure 8:
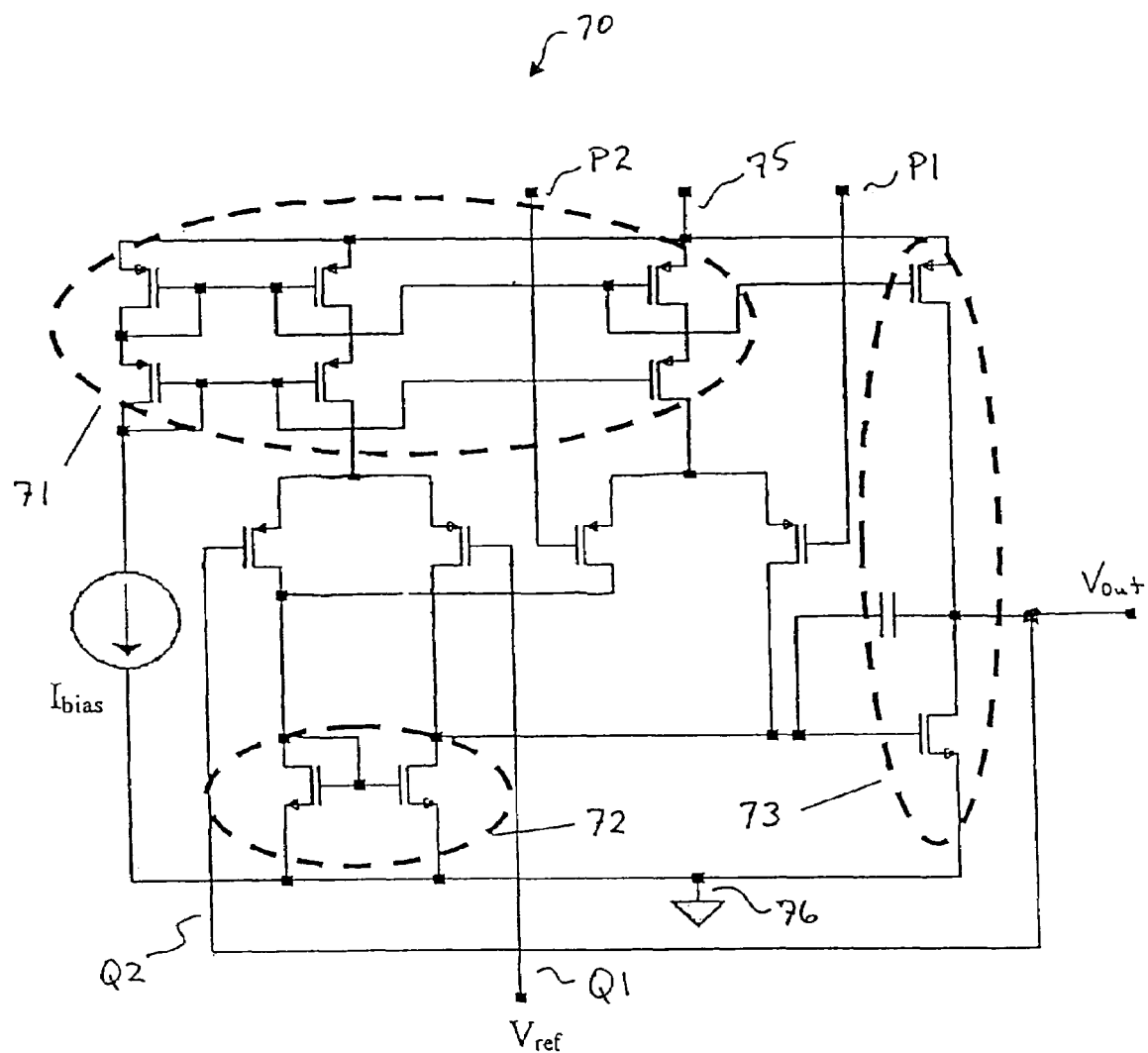
FIG. 8 is a schematic diagram showing an embodiment for the DDA of FIG. 7.

A DDA 70 which may be used to practice the invention is shown in FIG. 8. A power supply (not shown) supplies power at point 75. A ground 76 provides a path for return current flow. The direction of the current bias ($I_{bias}$) is indicated. Current sources 71 for each differential pair are implemented using a circuit configuration which embodies the cascode technique; see R. Gregorian and G. C. Temes, "*Analog MOS Integrated Circuits for Signal Processing*", John Wiley & Sons, 1986, pp. 131-133. The cascode technique provides good matching of the first (P1, P2) and second (Q1, Q2) differential pairs. This is desirable to achieve high performance of the DDA. Current mirror 72, converts the differential current of the differential pairs to a single-ended current, which is provided to the output stage 73.

For positive full-wave rectification, the DDA produces an output signal with voltage as follows (with half-wave rectification values in brackets):

If $V_{in} > V_{ref}$ then $V_{out} = V_{in}$

If $V_{in} < V_{ref}$ then $V_{out} = -V_{in}$ (or $V_{out} = V_{ref}$ for half-wave rectification).

For negative full-wave rectification, the DDA produces an output signal with voltage as follows (with half-wave rectification values in brackets):

If $V_{in} > V_{ref}$ then $V_{out} = -V_{in}$ (or $V_{out} = V_{ref}$ for half-wave rectification)

If $V_{in} < V_{ref}$ then $V_{out} = V_{in}$.

Since the situation where $V_{in}=V_{ref}$ is not important, a greater than equal condition ($\geq$) is equivalent to a greater than condition (>) and a less than equal condition ($\leq$) is equivalent to a less than condition (<). The DDA may optionally be configured to amplify its output signal by some gain factor.

As shown in the DDA equations above, when the source signal ($V_{in}$) is more positive than the reference signal ($V_{ref}$), the output signal ($V_{out}$) is equal to the source signal ($V_{in}$). When the source signal ($V_{in}$) is more negative than the reference signal ($V_{ref}$), the symmetric condition to the one described above happens, resulting in output signal ($V_{out}$) being equal to the negative value of the source signal ($-V_{in}$). Therefore, the output signal ($V_{out}$) is the positive rectified version of the source signal ($V_{in}$). Alternatively, if a negative rectified output is desired, the connections to the inputs 35, 36 of the polarity judgment circuit (C) can be reversed such that the source signal ($V_{in}$) is connected to the non-inverting input 36 and the reference signal ($V_{ref}$) is connected to the inverting input 35 of polarity judgment circuit (C). This alternate configuration yields the second set of DDA equations above for the negative full-wave (or half-wave) rectification.

Figure 9:
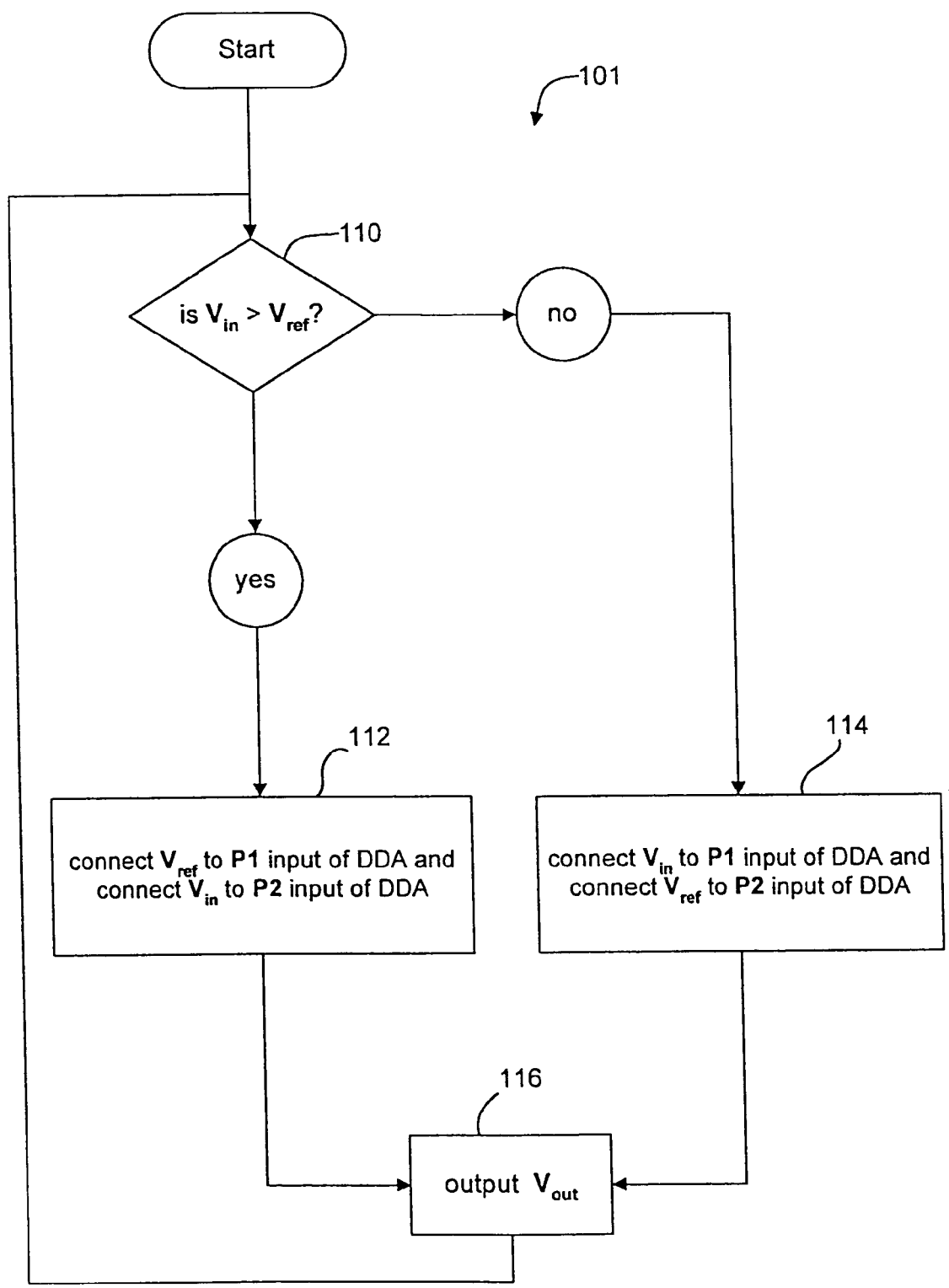
FIG. 9 is a flowchart showing a method according to the invention for positive full-wave rectification of a source signal.

FIG. 9 is a flowchart of a method 101 according to the invention for positive full-wave rectification of the source signal ($V_{in}$). The method begins at block 110 by comparing a source signal ($V_{in}$) to a reference signal ($V_{ref}$). If the source signal ($V_{in}$) is more positive than the reference signal ($V_{ref}$) then the method proceeds to block 112 where reference signal ($V_{ref}$) is connected to the first non-inverting input (P1) of the DDA and the source signal ($V_{in}$) is connected to the first inverting input (P2) of the DDA. If block 110 determines that the source signal ($V_{in}$) is not more positive than the reference signal ($V_{ref}$) then the method proceeds to block 114 where reference signal ($V_{ref}$) is connected to the first inverting input (P2) of the DDA and the source signal ($V_{in}$) is connected to the first non-inverting input (P1) of the DDA. The DDA produces an output signal at block 116. To achieve negative full-wave rectification, the greater than (>) condition in block 110 of method 101 can be replaced with a less than (<) condition, and vice versa.

Figure 10:
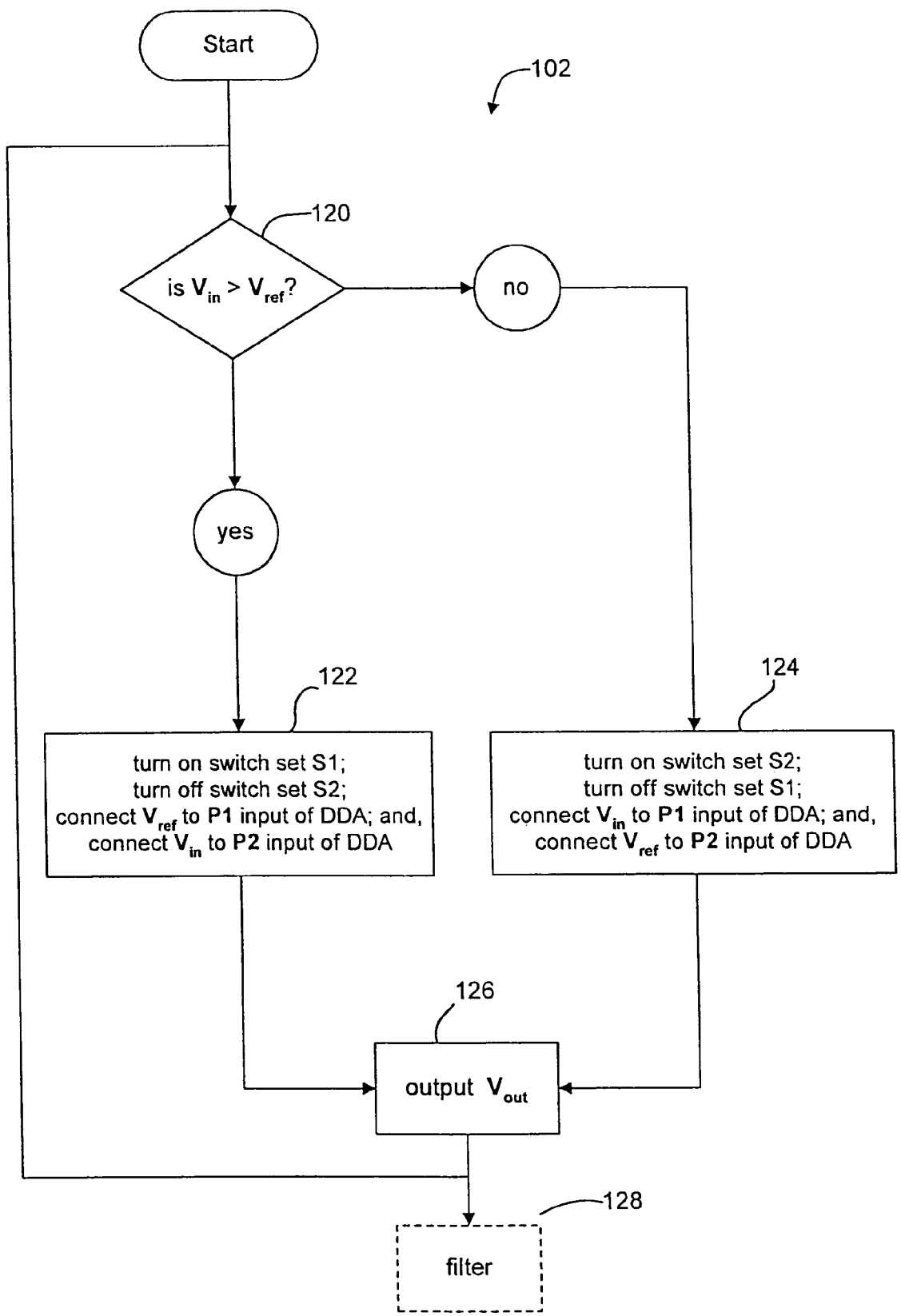
FIG. 10 is a flowchart showing a method according to the invention for positive full-wave rectification of a source signal in an embodiment with two sets of switching elements and an optional filter.

FIG. 10 is a flowchart of a method 102 according to a specific embodiment of the invention for full-wave positive rectification of a source signal ($V_{in}$). As with method 101, at block 120 method 102 compares the source signal ($V_{in}$) to the reference signal ($V_{ref}$). If the source signal ($V_{in}$) is more positive than the reference signal ($V_{ref}$) then, at block 122, the first switch set (S1) is turned on and the second switch set (S2) is turned off. Operation of the first switch set (S1) connects the reference signal ($V_{ref}$) to the first non-inverting input (P1) of the DDA and connects the source signal ($V_{in}$) to the first inverting input (P2) of the DDA. If block 120 determines that the source signal ($V_{in}$) is not more positive than the reference signal ($V_{ref}$) then the first switch set (S1) is turned off and the second switch set (S2) is turned on at block 124. Operation of the second switch set (S2) connects the reference signal ($V_{ref}$) to the first inverting input (P2) of the DDA and connects the source signal ($V_{in}$) to the first non-inverting input (P1) of the DDA. The DDA produces an output at block 126. The output may be conditioned by a filter or the like at block 128. As above, to achieve negative full-wave rectification, the greater than (>) condition in block 120 of method 102 can be replaced with a less than (<) condition, and vice versa. Method 102 further allows for an optional filter to be connected to the output of the DDA. The presence of a filter could smooth the output signal.

Figure 11:
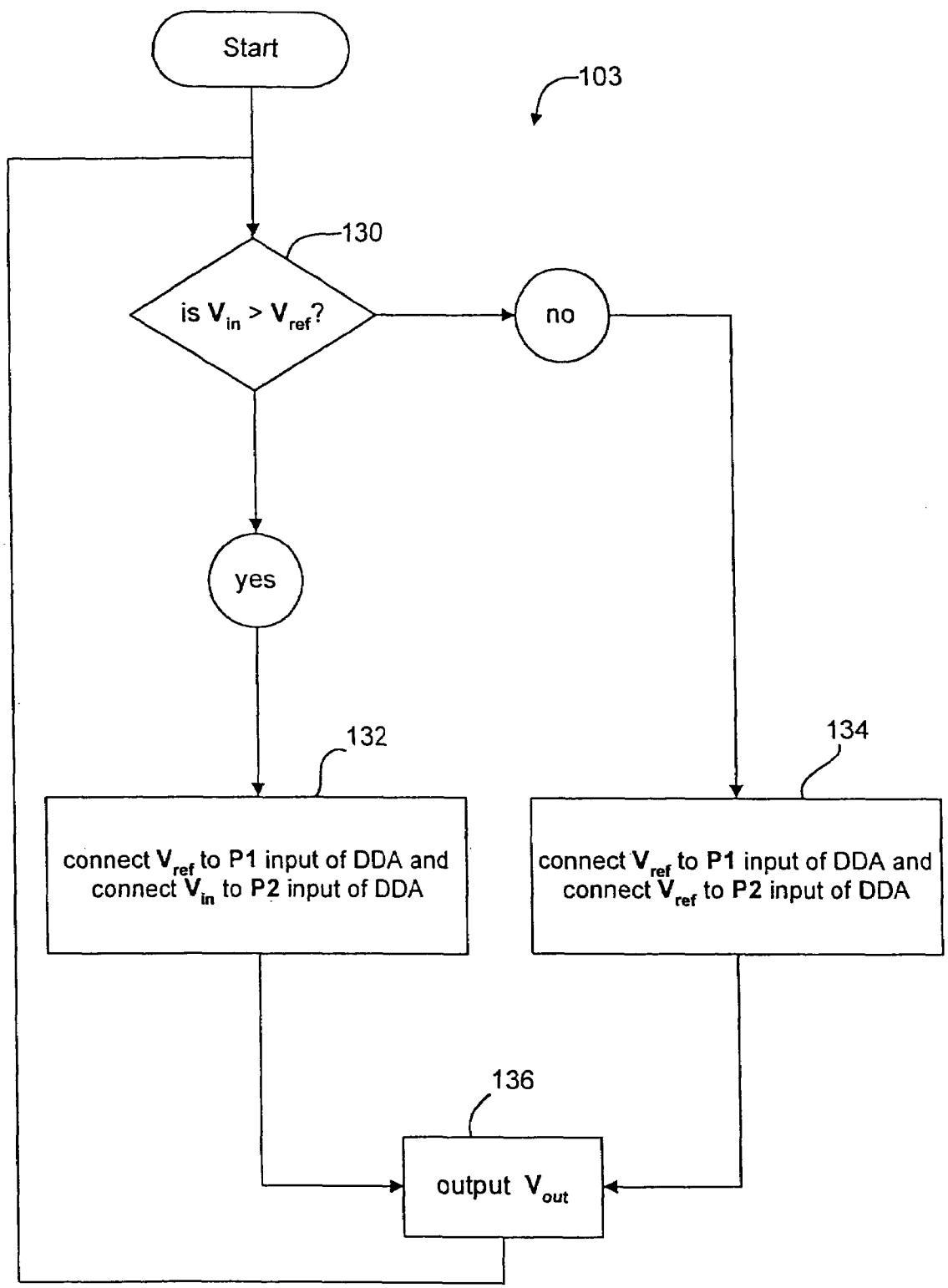
FIG. 11 is a flowchart showing a method according to the invention for positive half-wave rectification of a source signal.

FIG. 11 is a flowchart of a method 103 of the present invention for half-wave positive rectification of the source signal ($V_{in}$). As with methods 101 and 102, method 103 has a block 130 which compares the source signal ($V_{in}$) to the reference signal ($V_{ref}$). If block 130 determines that the source signal ($V_{in}$) is more positive than the reference signal ($V_{ref}$) then at block 132 reference signal ($V_{ref}$) is connected to the first non-inverting input (P1) of the DDA and the source signal ($V_{in}$) is connected to the first inverting input (P2) of the DDA. If block 130 determines that the source signal ($V_{in}$) is not more positive than the reference signal ($V_{ref}$) then at block 134, source signal ($V_{ref}$) is connected to the first non-inverting input (P1) and to the first inverting input (P2) of the DDA. The DDA provides output at block 136. To achieve negative half-wave rectification, the greater than (>) condition in block 130 of method 103 can be replaced with a less than (<) condition, and vice versa.

Preferred embodiments of the invention require only a small die area because it is not necessary to use any resistors or floating diodes. Consequently the invention can be fully integrated on a chip in CMOS technology. A low threshold voltage allows circuits according to the invention to be used to rectify low level bioelectrical signals such as signals picked up by nerve cuff electrodes. The full integration of a rectifying circuit having a low threshold voltage enables embodiments of the invention to be especially suitable for use in implantable biomedical devices. For example, a chip which bears a rectifier circuit according to the invention may be incorporated in an implantable device for rectifying nerve signals collected by electrodes for use in a system for manipulating a prosthetic device. A further benefit of requiring only a small die area is that several rectifier circuits of the invention can be integrated into the same implantable device together with other circuits. For example, one or more rectifying circuits according to the invention may be combined with one or more signal conditioning circuits such as amplifiers, filters, or the like on a single integrated circuit chip, which may be a CMOS chip.

As will be apparent to those skilled in the art in the light of the foregoing disclosure, many alterations and modifications are possible in the practice of the invention without departing from the spirit or scope thereof. For example:

the first and second switch sets (S1, S2) are each shown in the embodiment of FIG. 7 as comprising two switching elements, however the first and second switch sets (S1, S2) can be configured in a variety of ways, including as a plurality of switching elements, and any of FETs M1 M2, M3 or M4 may be replaced with other suitable electronic switches which, in their "ON" states offer sufficiently low thresholds. Accordingly, the scope of the invention is to be construed in accordance with the substance defined by the following claims.

What is claimed is:

1. A voltage rectifying circuit comprising:
a source signal input coupled to a first input of a polarity judgment circuit, to a first input of a first switch set and to a first input of a second switch set;
a reference signal input coupled to a second input of the polarity judgment circuit, to a second input of the first switch set, to a second input of the second switch set and to a second non-inverting input of a DDA;
the DDA having an output connected to a second inverting input of the DDA;
the polarity judgment circuit having an output connected to the input of an inverter and to a control input of the first switch set;
the inverter having an output connected to a control input of the second switch set;

the first switch set having a first output connected to a first non-inverting input of the DDA; and a second output connected to a first inverting input of the DDA; and the second switch set having a first output connected to the first non-inverting input of the DDA, and a second output connected to the first inverting input of the DDA.

2. A voltage rectifying circuit in accordance with claim 1, wherein the DDA comprises: current sources implemented using a cascode technique.

3. A voltage rectifying circuit in accordance with claim 2, wherein the polarity judgment circuit comprises a comparator.

4. A voltage rectifying circuit in accordance with claim 1, wherein the polarity judgment circuit comprises a comparator.

5. A voltage rectifying circuit comprising:

a source signal input coupled to a first input of a polarity judgment circuit, to a source of a first switching element and to a source of a third switching element;

a reference signal input coupled to a second input of the polarity judgment circuit, to a source of a second switching element, to a source of a fourth switching element and to a second non-inverting input of a DDA;

the DDA having an output connected to a second inverting input of the DDA;

the polarity judgment circuit having an output connected to the input of an inverter, to a gate of the second switching element and to a gate of the third switching element;

the inverter having an output connected to a gate of the first switching element and to a gate of the fourth switching element;

the first switching element having a drain connected to a first non-inverting input of the DDA;

the second switching element having a drain connected to the first non-inverting input of the DDA;

the third switching element having a drain connected to a first inverting input of the DDA; and, the fourth switching element having a drain connected to the first inverting input of the DDA.

6. A voltage rectifying circuit according to claim 5, wherein the switching elements are CMOS transistors.

7. A voltage rectifying circuit in accordance with claim 6, wherein the DDA comprises:

current sources implemented using a cascode technique.

8. A voltage rectifying circuit in accordance with claim 7, wherein the polarity judgment circuit comprises a comparator.

9. A voltage rectifying circuit according to claim 5, wherein the source of the first switching element is connected to the reference signal.

10. A voltage rectifying circuit according to claim 5, wherein the source of the third switching element is connected to the reference signal.

* * * * *